(12) United States Patent
Lopreato (10) Patent No.: US 7,829,502 B2
(45) Date of Patent: Nov. 9, 2010

(54) SYSTEMS AND METHODS FOR NUCLEASE-ASSISTED SELECTION AND ACQUISITION OF SINGLE STRANDED DNA OLIGOMER/POLYMER APTAMERS/LIGANDS

(76) Inventor: Gregory F. Lopreato, 12343 Hunters Chase Rd., #1411, Austin, TX (US) 78729

( * ) Notice: Subject to any disclaimer, the term of this patent is extended or adjusted under 35 U.S.C. 154(b) by 32 days.

(21) Appl. No.: 12/033,522

(22) Filed: Feb. 19, 2008

(65) Prior Publication Data

US 2010/0152056 A1    Jun. 17, 2010

Related U.S. Application Data

(60) Provisional application No. 60/903,243, filed on Feb. 22, 2007.

(51) Int. Cl.
*C40B 30/04* (2006.01)
*C40B 40/08* (2006.01)

(52) U.S. Cl. .......................................... 506/9; 506/16

(58) Field of Classification Search ....................... None
See application file for complete search history.

(56) References Cited

OTHER PUBLICATIONS

Wang (Aug. 24, 2004) Analytical Chemistry vol. 76 pp. 5605 to 5610.*
Kang (Dec. 9, 2004) Proceedings of the National Academy of Sciences USA vol. 101 pp. 17611 to 17615.*

* cited by examiner

*Primary Examiner*—Jeffrey S Lundgren
*Assistant Examiner*—Christian Boesen (57) ABSTRACT

A method for identifying aptamers that bind to target molecules may include contacting an oligonucleotide library with target molecule and digesting unbound oligonucleotides with one or more endonucleases, one or more exonucleases, or one or more endonucleases in combination with one or more exonucleases. A method for identifying aptamers may further include optionally subjecting selected aptamers to one or more rounds of selection under conditions of increased stringency. A method for identifying aptamers may include yet further amplifying selected aptamers. The described methods may be performed in a screen for identifying aptamers either alone or in combination with other methods typically employed in the art for selecting aptamers (such as, e.g., SELEX). Also contemplated herein are systems and kits for accomplishing the above.

16 Claims, 1 Drawing Sheet

SEQUENCE LISTING

```
<160> NUMBER OF SEQ ID NOS: 23

<210> SEQ ID NO 1
<211> LENGTH: 20
<212> TYPE: DNA
<213> ORGANISM: Artificial Sequence
<220> FEATURE:
<223> OTHER INFORMATION: Synthesized sequence
<220> FEATURE:
<221> NAME/KEY: misc_feature
<222> LOCATION: (20)..(20)
<223> OTHER INFORMATION: n is a, c, g, or t
```

```
<400> SEQUENCE: 1
gggggggttg gtggttggtn                                          20

<210> SEQ ID NO 2
<211> LENGTH: 14
<212> TYPE: DNA
<213> ORGANISM: Artificial Sequence
<220> FEATURE:
<223> OTHER INFORMATION: Synthesized sequence

<400> SEQUENCE: 2
ggttggtggt tggt                                                14

<210> SEQ ID NO 3
<211> LENGTH: 86
<212> TYPE: DNA
<213> ORGANISM: Artificial Sequence
<220> FEATURE:
<223> OTHER INFORMATION: Synthesized sequence

<400> SEQUENCE: 3
ggttggtggt tggtggttgg tgtggtgggg gggggggggg gggggggggg gggggggggg   60
gggggggggg tttttttttt tttttt                                       86

<210> SEQ ID NO 4
<211> LENGTH: 17
<212> TYPE: DNA
<213> ORGANISM: Artificial Sequence
<220> FEATURE:
<223> OTHER INFORMATION: Synthesized sequence
<220> FEATURE:
<221> NAME/KEY: misc_feature
<222> LOCATION: (17)..(17)
<223> OTHER INFORMATION: n is a, c, g, or t

<400> SEQUENCE: 4
ggggttggtg gttggtn                                             17

<210> SEQ ID NO 5
<211> LENGTH: 19
<212> TYPE: DNA
<213> ORGANISM: Artificial Sequence
<220> FEATURE:
<223> OTHER INFORMATION: Synthesized sequence

<400> SEQUENCE: 5
aaaaaaaaaa aaaaaaaaa                                           19

<210> SEQ ID NO 6
<211> LENGTH: 84
<212> TYPE: DNA
<213> ORGANISM: Artificial Sequence
<220> FEATURE:
<223> OTHER INFORMATION: Synthesized sequence

<400> SEQUENCE: 6
gttggtggtt ggtggttggt gtggttgggg gggggggggg gggggggggg gggggggggg   60
ggggggggtt tttttttttt tttt                                         84

<210> SEQ ID NO 7
<211> LENGTH: 86
<212> TYPE: DNA
<213> ORGANISM: Artificial Sequence
<220> FEATURE:
<223> OTHER INFORMATION: Synthesized sequence
```

<400> SEQUENCE: 7
ggttggtaaa aaaaaaaaaa aggggggggg ggggggggg ggggggggg ggggggggg     60 gggttttttt tttttttttg gttggt                                      86

<210> SEQ ID NO 8
<211> LENGTH: 21
<212> TYPE: DNA
<213> ORGANISM: Artificial Sequence
<220> FEATURE:
<223> OTHER INFORMATION: Synthesized sequence

<400> SEQUENCE: 8
ggttggtaaa aaaaaaaaaa a                                           21

<210> SEQ ID NO 9
<211> LENGTH: 23
<212> TYPE: DNA
<213> ORGANISM: Artificial Sequence
<220> FEATURE:
<223> OTHER INFORMATION: Synthesized sequence

<400> SEQUENCE: 9
accaaccaaa aaaaaaaaaa aaa                                         23

<210> SEQ ID NO 10
<211> LENGTH: 86
<212> TYPE: DNA
<213> ORGANISM: Artificial Sequence
<220> FEATURE:
<223> OTHER INFORMATION: Synthesized sequence

<400> SEQUENCE: 10
aaaaaaaaaa aaaaggttgg tggggggggg gggggggggg gggggggggg gggggggggg     60 ggggggttggt tttttttttt ttttt                                         86

<210> SEQ ID NO 11
<211> LENGTH: 18
<212> TYPE: DNA
<213> ORGANISM: Artificial Sequence
<220> FEATURE:
<223> OTHER INFORMATION: Synthesized sequence

<400> SEQUENCE: 11
aaaaaaaaaa aaaaggtt                                               18

<210> SEQ ID NO 12
<211> LENGTH: 24
<212> TYPE: DNA
<213> ORGANISM: Artificial Sequence
<220> FEATURE:
<223> OTHER INFORMATION: Synthesized sequence

<400> SEQUENCE: 12
aaaaaaaaaa aaaaaaccaa cccc                                        24

<210> SEQ ID NO 13
<211> LENGTH: 22
<212> TYPE: DNA
<213> ORGANISM: Artificial Sequence
<220> FEATURE:
<223> OTHER INFORMATION: Synthesized sequence -continued

```
<400> SEQUENCE: 13
ggttggtggt tggtgtgtgg tt                                              22

<210> SEQ ID NO 14
<211> LENGTH: 16
<212> TYPE: DNA
<213> ORGANISM: Artificial Sequence
<220> FEATURE:
<223> OTHER INFORMATION: Synthesized sequence

<400> SEQUENCE: 14
aaaaaaaaaa aaaaaa                                                     16

<210> SEQ ID NO 15
<211> LENGTH: 29
<212> TYPE: DNA
<213> ORGANISM: Artificial Sequence
<220> FEATURE:
<223> OTHER INFORMATION: Synthesized sequence

<400> SEQUENCE: 15
ggttggtggt tggtggttgg tgtggttgg                                       29

<210> SEQ ID NO 16
<211> LENGTH: 20
<212> TYPE: DNA
<213> ORGANISM: Artificial Sequence
<220> FEATURE:
<223> OTHER INFORMATION: Synthesized sequence
<220> FEATURE:
<221> NAME/KEY: misc_feature
<222> LOCATION: (20)..(20)
<223> OTHER INFORMATION: n is a, c, g, or t

<400> SEQUENCE: 16
gggggggttg gtggttggtn                                                 20

<210> SEQ ID NO 17
<211> LENGTH: 20
<212> TYPE: DNA
<213> ORGANISM: Artificial Sequence
<220> FEATURE:
<223> OTHER INFORMATION: Synthesized sequence

<400> SEQUENCE: 17
aaaaaaaaaa aaaaaaaaab                                                 20

<210> SEQ ID NO 18
<211> LENGTH: 44
<212> TYPE: DNA
<213> ORGANISM: Artificial Sequence
<220> FEATURE:
<223> OTHER INFORMATION: Synthesized sequence
<220> FEATURE:
<221> NAME/KEY: misc_feature
<222> LOCATION: (15)..(44)
<223> OTHER INFORMATION: n is a, c, g, or t

<400> SEQUENCE: 18
ggttggtggt tggtnnnnnn nnnnnnnnnn nnnnnnnnnn nnnn                      44

<210> SEQ ID NO 19
<211> LENGTH: 20
<212> TYPE: DNA
<213> ORGANISM: Artificial Sequence
<220> FEATURE:
<223> OTHER INFORMATION: Synthesized sequence
```

```
<220> FEATURE:
<221> NAME/KEY: misc_feature
<222> LOCATION: (20)..(20)
<223> OTHER INFORMATION: n is a, c, g, or t

<400> SEQUENCE: 19
gggggggttg gtggttggtn                                              20

<210> SEQ ID NO 20
<211> LENGTH: 15
<212> TYPE: DNA
<213> ORGANISM: Artificial Sequence
<220> FEATURE:
<223> OTHER INFORMATION: Synthesized sequence

<400> SEQUENCE: 20
ggttggtggt tggtg                                                   15

<210> SEQ ID NO 21
<211> LENGTH: 64
<212> TYPE: DNA
<213> ORGANISM: Artificial Sequence
<220> FEATURE:
<223> OTHER INFORMATION: Synthesized sequence
<220> FEATURE:
<221> NAME/KEY: misc_feature
<222> LOCATION: (15)..(64)
<223> OTHER INFORMATION: n is a, c, g, or t

<400> SEQUENCE: 21
ggttggtggt tggtnnnnnn nnnnnnnnnn nnnnnnnnnn nnnnnnnnnn nnnnnnnnnn    60 nnnn                                                                64

<210> SEQ ID NO 22
<211> LENGTH: 80
<212> TYPE: DNA
<213> ORGANISM: Artificial Sequence
<220> FEATURE:
<223> OTHER INFORMATION: Synthesized sequence
<220> FEATURE:
<221> NAME/KEY: misc_feature
<222> LOCATION: (15)..(64)
<223> OTHER INFORMATION: n is a, c, g, or t

<400> SEQUENCE: 22
ggttggtggt tggtnnnnnn nnnnnnnnnn nnnnnnnnnn nnnnnnnnnn nnnnnnnnnn    60 nnnnttttttt tttttttttt                                              80

<210> SEQ ID NO 23
<211> LENGTH: 16
<212> TYPE: DNA
<213> ORGANISM: Artificial Sequence
<220> FEATURE:
<223> OTHER INFORMATION: Synthesized sequence

<400> SEQUENCE: 23
ggggttggtg gttggt                                                  16
```

SYSTEMS AND METHODS FOR NUCLEASE-ASSISTED SELECTION AND ACQUISITION OF SINGLE STRANDED DNA OLIGOMER/POLYMER APTAMERS/LIGANDS

PRIORITY CLAIM

This application claims the benefit of priority of U.S. Provisional Patent Application Ser. No. 60/903,243 entitled "SYSTEMS AND METHODS FOR NUCLEASE-ASSISTED SELECTION AND ACQUISITION OF SINGLE STRANDED DNA OLIGOMER/POLYMER APTAMERS/LIGANDS", filed on Feb. 22, 2007.

BACKGROUND OF THE INVENTION

1. Field of the Invention

The present invention generally relates to the field of molecular biology. More specifically, the invention relates to systems and methods for rapid identification and enrichment of nucleic acid aptamers that bind to specific target molecules.

2. Description of the Related Art

Aptamers are nucleic acid molecules having specific binding affinity to molecules through interactions other than classic Watson-Crick base pairing.

Aptamers, like peptides generated by phage display or monoclonal antibodies (MAbs), are capable of specifically binding to selected targets and, through binding, block their targets' ability to function. Created by an in vitro selection process from pools of random sequence oligonucleotides, aptamers have been generated for over 100 proteins including growth factors, transcription factors, enzymes, immunoglobulins, and receptors. A typical aptamer is 10-15 kDa in size (30-45 nucleotides), binds its target with sub-nanomolar affinity, and discriminates against closely related targets (e.g., will typically not bind other proteins from the same gene family). A series of structural studies have shown that aptamers are capable of using the same types of binding interactions (hydrogen bonding, electrostatic complementarity, hydrophobic contacts, steric exclusion, etc.) that drive affinity and specificity in antibody-antigen complexes.

Aptamers have a number of desirable characteristics for use as therapeutics (and diagnostics) including high specificity and affinity, biological efficacy, and excellent pharmacokinetic properties. In addition, they offer specific competitive advantages over antibodies and other protein biologics, for example:

1) Speed and control. Aptamers are produced by an entirely in vitro process, allowing for the rapid generation of initial (therapeutic) leads. In vitro selection allows the specificity and affinity of the aptamer to be tightly controlled and allows the generation of leads against both toxic and non-immunogenic targets;

2) Toxicity and Immunogenicity. Aptamers as a class have demonstrated little or no toxicity or immunogenicity. In chronic dosing of rats or woodchucks with high levels of aptamer (10 mg/kg daily for 90 days), no toxicity is observed by any clinical, cellular, or biochemical measure. Whereas the efficacy of many monoclonal antibodies can be severely limited by immune response to antibodies themselves, it is extremely difficult to elicit antibodies to aptamers (most likely because aptamers cannot be presented by T-cells via the MHC and the immune response is generally trained not to recognize nucleic acid fragments;

3) Administration. Whereas all currently approved antibody therapeutics are administered by intravenous infusion (typically over 2-4 hours), aptamers can be administered by subcutaneous injection. This difference is primarily due to the comparatively low solubility and thus large volumes necessary for most therapeutic MAbs. With good solubility (>150 mg/ml) and comparatively low molecular weight (aptamer: 10-50 kDa; antibody: 150 kDa), a weekly dose of aptamer may be delivered by injection in a volume of less than 0.5 ml. Aptamer bioavailability via subcutaneous administration is >80% in monkey studies (Tucker et al., J. Chromatography B. 732: 203-212, 1999). In addition, the small size of aptamers allows them to penetrate into areas of conformational constrictions that do not allow for antibodies or antibody fragments to penetrate, presenting yet another advantage of aptamer-based therapeutics or prophylaxis;

4) Scalability and cost. Therapeutic aptamers are chemically synthesized and consequently can be readily scaled as needed to meet production demand. Whereas difficulties in scaling production are currently limiting the availability of some biologics and the capital cost of a large-scale protein production plant is enormous, a single large-scale synthesizer can produce upwards of 100 kg oligonucleotide per year and requires a relatively modest initial investment; and 5) Stability. Therapeutic aptamers are chemically robust. They are intrinsically adapted to regain activity following exposure to heat, denaturants, etc. and can be stored for extended periods (>1 yr) at room temperature as lyophilized powders. In contrast, antibodies must be stored refrigerated.

SELEX is a very powerful and novel technique used to search (i.e., pan) for aptamers exhibiting high-affinity and specific binding to target molecules of biomedical interest. SELEX searches a very large, random sequence oligonucleotide library (on the order of $10^{12}$ to $10^{15}$) for molecules exhibiting high-affinity binding to defined molecular targets. The small number of selected (i.e., high binding affinity) oligonucleotides can be geometrically amplified using the polymerase chain reaction (PCR) in a few weeks (or days with the use of robotics). Through a "survival of the fittest" sequential screening strategy (i.e., those having the highest binding affinity or catalytic activity) identification of novel aptamers can be accomplished rapidly in vitro using SELEX.

Despite its utility, SELEX is a laborious process requiring the physical separation of target bound aptamers and multiple rounds of sequential selection and amplification (Gold et al., 1995; Cox et al., 2002a, 2002b; Chambers et al. 2001, 2002; lqbal et al. 1999, 2000a, 2003; Bruno and Kiel, 1999, 2002; Vivekananda and Kiel, 2006). Consequently, elaborate robotics stations are routinely employed to run SELEX, and this sort of instrumentation is beyond the attainment of the average lab.

Consequently a need exists for rapid and efficient methods of aptamer selection that does not require sophisticated instrumentation, and that may be performed routinely in an average lab.

SUMMARY OF THE INVENTION

In an embodiment, a method of identifying nucleic acid aptamers for a target molecule may include obtaining an at least partially purified target molecule, obtaining a nucleic acid ligand library, mixing the target molecule with the nucleic acid ligand library and binding the target molecule to one or more aptamers present in the nucleic acid ligand library, and digesting unbound nucleic acid molecules with one or more endonucleases, with one or more exonucleases, or with one or more endonuclease in combination with one or more exonucleases.

In an embodiment, a method of identifying nucleic acid aptamers for a target molecule may include obtaining an at least partially purified target molecule, obtaining a nucleic acid ligand library, mixing the target molecule with the nucleic acid ligand library and binding the target molecule to one or more aptamers molecules present in the nucleic acid ligand library, separating the aptamers bound to the target molecule from at least a portion of the unbound nucleic acid molecules, wherein said separating step is accomplished by: digesting unbound oligonucleotides, or digesting unbound oligonucleotides in combination at least one physical separation means, liberating the target molecule from the aptamers, and amplifying the aptamers.

Still further embodiments concern kits suitable for the purpose of performing a screen for aptamers that bind to a molecule of interest. The kits include, in at least a first suitable container, a suitable oligonucleotide library, one or more endonucleases, and one or more 3'→5' exonucleases, in conjunction with instructions for use in performing a screen for aptamers that bind to a molecule of interest. A kit may optionally further contain one or more appropriate binding buffers, and/or one or more buffers suitable to enable activity of the provided nucleases. The kit may further contain one or more reagents, including suitable buffer, enzymes and primers, for amplifying selected aptamers by PCR.

BRIEF DESCRIPTION OF THE DRAWINGS

The above brief description as well as further objects, features and advantages of the methods and apparatus of the present invention will be more fully appreciated by reference to the following detailed description of presently preferred but nonetheless illustrative embodiments in accordance with the present invention when taken in conjunction with the accompanying drawings in which:

FIG. 1 is an overview of a Knockdown Nuclease Protected Aptamer Selection and Acquisition ("KN-PASA") performed in accordance with one embodiment.

While the invention is susceptible to various modifications and alternative forms, specific embodiments thereof are shown by way of example in the drawings and well herein be described in detail. It should be understood, however, that the drawing and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Definitions

It is to be understood that the present invention is not limited to particular devices or biological systems, which may, of course, vary. It is also to be understood that, as used in this specification and the appended claims, the singular forms "a", "an", and "the" include singular and plural referents unless the content clearly dictates otherwise. Thus, for example, reference to "a linker" includes one or more linkers. It is to be yet further understood that any terminology used herein is for the purpose of describing particular embodiments only, and is not intended to be limiting.

The terms used throughout this specification generally have their ordinary meanings in the art, within the context of the invention, and in the specific context where each term is used. Certain terms are discussed below, or elsewhere in the specification, to provide additional guidance to the practitioner in describing the general embodiments of the invention, as well as how to make and use them. It will be readily appreciated that the same thing can be said in more than one way. Consequently, alternative language and synonyms may be used for any one or more of the terms discussed herein, nor is any special significance to be placed upon whether or not a term is elaborated or discussed in greater detail herein. Synonyms for certain terms are provided. A recital of one or more synonyms does not exclude the use of other synonyms. The use of examples anywhere in this specification, including examples of any terms discussed herein, is illustrative only, and in no way limits the scope and meaning of the invention or of any exemplified term.

As used herein, the term "Knockdown Nuclease Protected Aptamer Selection and Acquisition" or "KN-PASA" is generally used to describe at least a portion of the methods and systems that form the basis of the present disclosure. The term derives from an aspect of the methods described below, in which nucleases (in particular, certain endonuclease and certain exonucleases) are employed to remove (i.e., "knockdown") oligonucleotide molecules, from a library, that do not interact with a target molecule.

As used herein, the term "aptamers" generally refers to nucleic acid molecules having specific binding affinity to target molecules through interactions other than classic Watson-Crick base pairing. Aptamers are usually identified by selecting them from a large random sequence pool, but natural aptamers also exist in riboswitches. Aptamers can be used for both basic research and clinical purposes as macromolecular drugs. Aptamers can be combined with ribozymes to self-cleave in the presence of their target molecule. These compound molecules have additional research, industrial and clinical applications. More specifically, aptamers can be broadly classified as either nucleic acid (DNA or RNA) aptamers, which consist of (usually short) strands of oligonucleotides, or peptide aptamers, which consist of a short variable peptide domain, attached at both ends to a protein scaffold. Aptamers, like peptides generated by phage display or monoclonal antibodies (MAbs), are capable of specifically binding to selected targets and, through binding, block or otherwise alter the function of the target molecule to which they bind. Aptamers are typically identified by an in vitro selection process (such as, e.g., SELEX) from pools of random sequence oligonucleotides. Aptamers have been generated for over 100 proteins including growth factors, transcription factors, enzymes, immunoglobulins, and receptors. A typical aptamer is 10-15 kDa in size (30-45 nucleotides), binds its target with sub-nanomolar affinity, and discriminates against closely related targets (e.g., will typically not bind other proteins from the same gene family). Aptamers have a number of desirable characteristics for use as therapeutics including high specificity and affinity, biological efficacy, and excellent pharmacokinetic properties. While it will readily appreciated by a practitioner of the art that peptide aptamers also exist, such aptamers are beyond the scope of the present description. Aptamers, their uses and manufacture are shown in U.S. Pat. Nos. 5,582,981; 5,631,146; 5,756,291; 5,780,449; 5,792,613; 5,840,867; 5,861,501; 6,001,648; 6,111,095; 6,207,388; 6,225,058; 6,369,208; 6,423,493; 6,458,559; 6,515,120; 6,569,630; 6,706,481; 6,780,850; 6,858,390; 6,867,289; 6,949,379; 6,994,959, as well as U.S. Patent Appl. Publ. Nos. 2007/0027096; 2007/0020641; 2007/

0009476; 2006/0281702; 2006/0264369; 2006/0257915; 2006/0257914; 2006/0205089; 2006/0193821; 2006/0183702; 2006/0172925; 2006/0148745; 2006/0128649; 2006/0121489; 2006/0105980; 2006/0105975; 2006/0088864; 2006/0084109; 2006/0068407; 2006/0030535; 2006/0024814; 2006/0018871; 2006/0014172; 2006/0008841; 2005/0282226; 2005/0282190; 2005/0260164; 2005/0250106; 2005/0239134; 2005/0233317; 2005/0222400; 2005/0214772; 2005/0176940; 2005/0159351; 2005/0142582; 2005/0124565; 2005/0123939; 2005/0106594; 2005/0096290; 2005/0089864; 2005/0078179; 2005/0053970; 2004/0265912; 2004/0253679; 2004/0253243; 2004/0249130; 2004/0242521; 2004/0180360; 2004/0137429; 2004/0137010; 2004/0110235; 2004/0086924; 2004/0053310; 2004/0023266; 2004/0022727; 2003/0219801; 2003/0175730; 2003/0175703; 2003/0162190; 2003/0138831; 2003/0119159; 2003/0108532; 2003/0064530; 2003/0027184; 2003/0022853; 2002/0197617; 2002/0127581; 2002/0115629; 2002/0037506; and 2001/0046674, all of which are hereby expressly incorporated by reference in their entirety as though fully set forth herein.

As used herein, the term "polynucleotide" generally refers to a naturally occurring, recombinant or synthetic polymer of nucleotides (which contain sugar groups, and either purine or pyrimidine bases) that are covalently linked by sequential phosphodiester bonds. There are generally two types of polynucleotide: ribonucleic acid (RNA) and deoxyribonucleic acid (DNA). The bases involved are adenine, guanine, cytosine, and thymine (abbreviated A, G, C. and T, respectively) or uracil (abbreviated U) (in the case of RNA). Some nucleic acids may be informational biomolecules (e.g., DNA), or act as agent (e.g., RNA) in causing that information to be expressed (e.g., as a protein, or by its involvement in RNA-interference). For the purposes of the present disclosure, the terms "polynucleotide" and "nucleic acid" may generally be used interchangeably.

As used herein, the terms "isolated polynucleotide" or "isolated nucleic acid" generally refer to a polynucleotide, or a fragment thereof, that is free of the genetic material that, in the naturally occurring genome of the organism from which the nucleic acid is derived, flank the polynucleotide. The term therefore encompasses, for example, a DNA fragment that is incorporated, using recombinant DNA methodologies, into a vector; into an autonomously replicating plasmid or virus; or into the genome of a prokaryote or eukaryote; or that exists as a separate molecule (e.g., an oligonucleotide, siRNA duplexes, a cDNA or a genomic or cDNA fragment produced by PCR or restriction endonuclease digestion) independent of other sequences. It also includes recombinant DNA that is part of a hybrid gene encoding additional polypeptide sequence(s) (e.g. a fusion protein) or an adapter sequence.

As used herein, the term "substantially identical", when used in reference to a polynucleotide, generally refers to a polynucleotide, or a portion or fragment thereof, whose nucleotide sequence is at least 95%, 90%, 85% 80%, 70%, 60% or 50% identical to the nucleotide sequence of a reference polynucleotide. When used in reference to a polypeptide, the term generally refers to a polypeptide, or a fragment thereof, whose amino acid sequence is at least 95%, 90%, 85% 80%, 70%, 60% or 50% identical to the amino acid sequence of a reference polypeptide. For polypeptides, the length of comparison sequences will generally be at least about 5 amino acids, and may include the complete polypeptide sequence. For nucleic acids, the length of comparison sequences will generally be at least about 15 nucleotides, and may include the complete reference nucleic acid sequence.

Sequence identity between two or more polypeptide or nucleic acid sequences is typically determined using sequence analysis software (e.g., Sequence Analysis Software Package of the Genetics Computer Group, University of Wisconsin Biotechnology Center) designed for this purpose. Such software matches similar sequences by assigning degrees of homology to various substitutions, deletions, substitutions, and other modifications. Conservative substitutions typically include substitutions within the following groups: Gly; Ala; Val, Ile, Leu; Asp, Glu, Asn, Gln; Ser, Thr; Lys, Arg; and Phe, Tyr.

As used herein, the term "polymerase chain reaction" (commonly referred to in the art as "PCR") generally refers to a method, or a modification thereof, for increasing the concentration of a segment of a target DNA sequence in a mixture of DNA containing the target sequence. Examples of PCR methods are shown in U.S. Pat. Nos. 4,683,195 4,683,202, and 4,965,188, all of which are incorporated herein by reference. Broadly speaking, PCR techniques are used to amplify a region of DNA interspersing two known DNA sequences. Collectively, the interspersing region of DNA and its flanking regions is known as an "amplicon". Two primers, a sense primer having a sequence identical or substantially identical to one end of the amplicon, and an anti-sense primer having a sequence that is the reverse complement or substantial reverse complement of the other end of the amplicon, are synthesized. The sense and anti-sense primers may be anywhere from about 5 to about 100 nucleotides in length, though other length may be possible as well. For most routine applications, the primers are typically between about 8 to about 30 nucleotides in length. PCR is usually is performed for about 20 to about 35 cycles, though more or fewer cycles may be performed depending on the specifics of the application and the desired outcome. Most commonly, each PCR cycle is carried out in three steps, often preceded by one temperature hold at the start and followed by one hold at the end.

Prior to the first cycle, during an initialization step, the PCR reaction is often heated to a temperature of 94-96° C. (or 98° C. if extremely thermostable polymerases are used), and this temperature is then held for about 1 to about 10 minutes. This first hold is employed to ensure that most of the DNA template and primers are denatured, i.e., that the DNA is melted by disrupting the hydrogen bonds between complementary bases in two DNA strands. Also, some PCR polymerases require this step for activation (i.e., a "hot-start PCR"). Following this hold, cycling begins, with one step at 94-98° C. for 20-30 seconds (denaturation step).

The denaturation is followed by an annealing step. In this step the reaction temperature is lowered so that the primers can bind to the complementary region of the denatured (i.e., single stranded) DNA template. The temperature at this step depends on the $T_m$ of the primers (see above), and is usually between 50-64° C. for 20-40 seconds.

The annealing step is followed by an extension/elongation step during which the DNA polymerase copies the DNA template, starting at the primers annealed to both of its strands. The temperature at this step depends on the DNA polymerase used. Taq polymerase has a temperature optimum of 70-74° C.; thus, in most cases, during the extension a temperature of 72° C. is used, though of course as will readily be appreciated by the practitioner, other polymerases are available and may be used as well. The final conditions of the PCR reaction will depend on a number of factors including but not limited to the identity of the polymerase employed in the procedure. The extension time depends both on the DNA polymerase used and on the length of the DNA fragment to be amplified. As a practical rule-of-thumb, at its optimum temperature, the DNA polymerase will polymerize a thousand bases in one minute. A final elongation step is frequently used after the last cycle to ensure that any remaining single-stranded DNA is completely copied. This differs from the other elongation steps only in that it is longer—typically 10-15 minutes. A final hold of 4-15° C. for an indefinite time is often employed to allow short-term storage of the reaction, especially if reactions are run overnight, and cannot be removed immediately after the cycling.

The term "real-time PCR," "quantitative PCR" or "qPCR" generally refers to modified PCR procedure in which the starting amount of target DNA, cDNA or RNA relative to other molecules in a mixture can be determined. QPCR uses fluorescent signals that are generated during the PCR procedure to calculate the amount of initial template present in a biological sample. QPCR is commonly used in the art to determine the relative expression levels of one or more genes of interest.

As used herein, the terms "PCR product", "PCR fragment" or "amplicon" generally refer to the resultant mixture of amplified DNA after two or more cycles of the PCR steps of denaturation, annealing and extension are complete. The sequence of an amplicon includes the amplified segment of DNA as well as the sequence of the primers flanking the amplified region that were employed to carry out the PCR. These terms are also meant to encompass the case where there has been amplification of one or more segments of one or more target sequences.

As used herein, the term "primer" generally refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (e.g., in the presence of nucleotides and an inducing agent such as DNA polymerase and at a suitable temperature and pH). The primer is preferably single stranded for maximum efficiency in applications involving PCR amplification, but may alternatively, be double stranded. If double stranded, the primer is first treated to separate its strands before being used to prepare extension products. The primer must be sufficiently long to prime the synthesis of extension products in the presence of the inducing agent. The exact lengths of the primers will depend on many factors, including annealing temperature, source of primer and the method used, all of which are readily appreciated and understood by a practitioner of ordinary skill in the art to which the present invention pertains.

As used herein, the term "oligonucleotide" (sometimes referred to simply as "oligo") generally refers to a nucleic acid molecule whose nucleic acid sequence typically comprises up to 200 nucleotides, more typically <100 nucleotides, and most typically <50 nucleotides. Oligos are commonly referred to as "N"-mers, where "N" denotes the number of bases comprising the oligo. Thus, an oligo having a sequence of 25 bases may be referred to as a 25-mer. Furthermore, oligos may be covalently modified such as, e.g., coupled to a dye, a marker, a protein, a functional group, sugars etc. Oligos may also be covalently modified (e.g., phosphorylated or dephosphorylated) at either the 5' or 3' end using a variety of chemical techniques or commercially available enzymes (e.g., kinases or phosphatases). Under the appropriate conditions (typically in aqueous solutions of appropriate temperature, pH and ionic strength) reference oligos, or sequences found within the oligos, may be made to bind to an oligo or sequences of an oligo having a sequence complementary to that of the reference oligo. It should be noted that the terms "oligonucleotide" and "polynucleotide" are both used to refer to nucleic acid molecules, the difference being that, whereas the term "oligonucleotide" is used in reference to relatively short nucleic acid molecules, the term "polynucleotide" may be used in reference to all nucleic acid molecules, irrespective of their length. Nevertheless, as will be readily appreciated by the skilled artisan, use of the terms "oligonucleotide" and "polynucleotide" in referring to "long" vs. "short" molecules may be subjective. Thus, it is to be understood that unless specified to the contrary, the terms "oligonucleotide" and "polynucleotide" may, for the purposes of the present disclosure be used interchangeably.

The term "complementary," when used in the context of a nucleic acid sequence is a well-known term of the biological arts that refers to a nucleic acid sequence that has an opposite orientation to, and is capable of forming Watson-Crick base pairs with, a reference nucleic acid sequence. Since there is only one complementary base for any of the bases found in DNA and in RNA, one can reconstruct a complementary nucleic acid sequence for any single nucleic acid sequence. The term "substantially complementary" generally means a nucleotide sequence that is complementary to at least 80%, at least 85%, at least 90%, at least 95%, or at least at least 98% of a reference nucleotide sequence. Oligonucleotides may be made using a variety of enzymatic methods, such as, PCR, primer extension, restriction digestion. Alternatively, oligonucleotides may be made using a variety of chemical techniques. Most typically, custom oligonucleotides (i.e., oligonucleotides having customer specified sequence, length and any chemical modifications) are synthesized commercially using automated DNA/RNA synthesizers, which allow for the routine synthesis of oligonucleotides up to about 200 nucleotides in length having specified or randomized sequence. Oligonucleotide synthesis and design is a highly developed art, and the properties and general uses of these molecules well known to practitioners of the biological arts. Several computer algorithms are available which aid in the design, analysis and selection of oligonucleotides and include, by way of non-limiting example, programs such as "Osprey" (described in "Osprey: a comprehensive tool employing novel methods for the design of oligonucleotides for DNA sequencing and microarrays." Gordon et al., Nucleic Acids Research 2004 32(17)); GENEWALKER™ (by CYBERGENE™ AB; http://www.cybergene.se); GeneFischer (http://bibiserv.techfak.uni-bielefeld.de/genefisher/); CLCBIO™ (http://www.clcbio.com); and The OligoFaktory (described in "OligoFaktory: a visual tool for interactive oligonucleotide design." Schretter et al., Bioinformatics. 2006 Jan. 1; 22(1):115-6) among many others. Oligonucleotide synthesis and design services are available from a number of commercial entities such as, by way of non-limiting example only, INVITROGEN®, BIONEER® INC., BIOSEARCH TECHNOLOGIES®, EXIQON®, IDAHO TECHNOLOGY® INC., LC SCIENCES®, MIDLAND CERTIFIED REAGENT COMPANY®, SBS GENETECH®, THERMO SCIENTIFIC®, YORKSHIRE BIOSCIENCE® LTD, ALPHA DNA®, MICROSYNTH® AG, BIOSERVE®, BIO-SYNTHESIS®, EUROGENTEC EXPRESSON BIO-SYSTEMS® LTD., FAVORGEN BIOTECH® CORP., IBA® GMBH, ILLUMINA® MWG, BIOTECH OLIGO FACTORY®, OLIGOS ETC.® INC., OPERON BIOTECHNOLOGIES® INC., PROLIGO®, RETROGEN®, ROCKLAND IMMUNOCHEMICALS® INC., and SEQWRIGHT®.

As used herein, the term "recombinant," when used in reference to a polynucleotide or a protein, generally refers to a polynucleotide or a polypeptide molecule that is produced using genetic engineering techniques and that is distinct from a naturally occurring nucleic acid or polypeptide molecule. Recombinant DNA (sometimes represented as "rDNA") is an artificial DNA sequence resulting from the combining of two other DNA sequences in a plasmid/vector. The term recombinant DNA refers to a new combination of DNA molecules that are not found together naturally. Although processes such as crossing over (genetic recombination) technically produce recombinant DNA, the term is generally reserved for DNA produced by joining molecules derived from different biological sources.

The term "portion", as used herein, in the context of a molecule, such as a polypeptide or of a polynucleotide (as in "a portion of a given polypeptide/polynucleotide") generally refers to fragments of that molecule. The fragments may range in size from three amino acid or nucleotide residues to the entire molecule minus one amino acid or nucleotide. Thus, for example, a polypeptide "comprising at least a portion of the polypeptide sequence" encompasses the polypeptide defined by the sequence, and fragments thereof, including but not limited to the entire polypeptide minus one amino acid.

As used herein, the term "Systematic Evolution of Ligands by Exponential Enrichment" or "SELEX" generally refers to a combinatorial technique used in molecular biological for producing oligonucleotides of either single-stranded DNA or RNA ligands that specifically bind to a target molecule. The selected sequences are referred to as aptamers. Very broadly, the process begins with the synthesis of a very large oligonucleotide library consisting of randomly generated sequences of fixed length flanked by constant 5' and 3' ends that serve as sequences suitable for primer binding and amplification. For a randomly generated region of length n, the number of possible sequences in the library is $4^n$. The sequences in the library are exposed to the target molecule—which may be a protein or small organic or inorganic compound—and those that do not bind the target even weakly are removed, usually by affinity chromatography. The bound sequences are isolated and amplified by PCR to prepare for subsequent rounds of selection in which the stringency of the elution conditions is increased (i.e., by changing incubation temperature, ionic concentration, or by adding a weak denaturant) to identify the highest-affinity sequences. The technique has been used to evolve aptamers of extremely high binding affinity to a variety of target molecules, including small molecules such as ATP and adenosine as well as proteins such as prions and vascular endothelial growth factor (VEGF). Clinical uses of the technique are suggested by aptamers that bind tumor markers. For example, clinical trials are underway for a VEGF-binding aptamer trade-named Macugen in treating macular degeneration. One caution advanced in relation to the method emphasizes that selection for extremely high, sub-nanomolar binding affinities may not in fact improve specificity for the target molecule. Off-target binding to related molecules could have significant clinical effects (see, e.g., Dieckmann et al., (1996). Solution structure of an ATP-binding RNA aptamer reveals a novel fold. *RNA* 2(7):628-40; Huizenga et al. (1995). A DNA aptamer that binds adenosine and ATP. *Biochemistry* 34(2):656-65; Mercey et al., (2006) Fast, reversible interaction of prion protein with RNA aptamers containing specific sequence patterns. *Arch Virol* 151(11):2197-214; Burke D H, Gold L. (1997). RNA aptamers to the adenosine moiety of S-adenosyl methionine: structural inferences from variations on a theme and the reproducibility of SELEX. *Nucleic Acids Res* 25(10): 2020-4; Ulrich et al., (2006). DNA and RNA aptamers: from tools for basic research towards therapeutic applications. *Comb Chem High Throughput Screen* 9(8):619-32); Ferreira et al., (2006). DNA aptamers that bind to MUC1 tumour marker: design and characterization of MUC1-binding single-stranded DNA aptamers. *Tumour Biol* 27(6):289-301; Vavvas et al., (2006). Pegaptanib (Macugen): treating neovascular age-related macular degeneration and current role in clinical practice. *Ophthalmol Clin North Am.* 19(3):353-60; Carothers et al., (2006). Aptamers selected for higher-affinity binding are not more specific for the target ligand. *J Am Chem Soc* 128(24):7929-37). Methods and variations thereof for performing SELEX are also described in detail in U.S. Pat. Nos. 7,176,295; 6,855,496; 6,730,482; 6,706,482; 6,613,526; 6,506,887; 6,465,189; 6,387,620; 6,376,474; 6,376,190; 6,300,074; 6,291,184; 6,261,774; 6,114,120; 6,083,696; 6,030,776; 6,013,443; 6,001,577; 5,998,142; 5,962,219; 5,864,026; 5,861,254; 5,858,660; 5,789,160; 5,789,157; 5,773,598; 5,763,595; 5,763,566; 5,763,177; 5,723,592; 5,723,289; 5,712,375; 5,705,337; 5,683,867; 5,637,459; and 5,567,588, as well as U.S. Patent Application Publication Nos. 2006/0088877; 2005/0136474; 2004//0132067; 20030099945; 2003/0087301; 2003/0077646; 2003/0044818; 2003/0027781; 2003/0003461; 2002/0106652; 2002/0102599. The text of the foregoing references and patent publications are hereby expressly incorporated by reference in their entirety as though fully set forth herein.

As used herein, the term "separating" when used in the context of target molecule/aptamer selection methods, generally means separation of oligonucleotide/target complexes, preferably DNA/protein complexes, from the surrounding pool of unbound oligonucleotides. This may be accomplished using one or more physical separation means, such as, by way of various non-limiting examples, affinity chromatography (e.g., biotin/avidin, antibody affinity, metal ion affinity chromatography, or using a target molecule-fusion protein such as glutathione S-transferase, Maltose Binding Protein, or the like); filtration; magnetic bead separation, centrifugation, chemical extraction, or any of the methods described in the aforementioned patents and incorporated herein, or by enzymatic means (such as, e.g., enzymatic hydrolysis of unbound oligonucleotides).

The terms "5'" and "3'," when used in the context of a reference nucleic acid molecule, are generally used to indicate the directionality of the nucleic acid molecule. The chemical convention of naming carbon atoms in the nucleotide sugar-ring numerically gives rise to a 3' end and a 5' end. The relative positions of structures along a strand of nucleic acid, including genes, transcription factors, and polymerases are usually noted as being either upstream (towards the 5' end) or downstream (towards the 3' end). The importance of having this type of naming convention is easily demonstrated by the fact that nucleic acids can only be synthesized in vivo in a 5' to 3' direction, as the polymerase used to construct new strands must attach a new nucleotide to the 3' hydroxyl (—OH) group via a phosphodiester bond. For this and other reasons, DNA and RNA sequences are conventionally written starting from the 5' end of the molecule, and proceeding to the 3' end. Thus, the reference sequence GGATTC, for example, is the convention used to represent a DNA molecule having the structure 5'OH-GGATTC-3'OH. Conversely, it's reverse complement (i.e., a sequence that would, under the appropriate conditions, form Watson-Crick base pairing with this reference sequence is GAATCC, and represents the structure 5'OH-GAATCC-3'OH.

As used herein, the term "endonuclease" generally refers to a class of enzymes that cleave phosphodiester bonds within a polynucleotide chain. Restriction endonucleases (restriction enzymes) cleave DNA at or near specific recognition sites (sequences). Non-specific endonucleases, on the other hand, cleave DNA or RNA into mono-, di-, tri-, or oligonucleotide products. Exemplary non-specific endonucleases include DNase I, S1 Nuclease, Nuclease Bal31 (which is also an exonuclease), Mung-bean nuclease, T7 Endonuclease I.

As used herein, the term "exonuclease" generally refers to a class of enzymes that cleave nucleotides one at a time from an end of a polynucleotide chain. These enzymes hydrolyze phosphodiester bonds from either the 3' or 5' terminus of polynucleotide molecules. Exonucleases that hydrolyze nucleotides from the 5' end of a nucleic acid molecule may generally be referred to as a 5'→3' exonucleases. Examples of 5'→3' exonucleases include, by way of illustration only, λ-exonuclease, T7 Exonuclease, and RecJ. Exonucleases that hydrolyze nucleotides from the 3' end of a nucleic acid molecule may generally be referred to as a 3'→5' exonucleases. Illustrative examples of 3'→5' exonucleases include Exonuclease I, Exonuclease III, and Exonuclease T. Nuclease Bal31, which also functions as an endonuclease, is both a 5'→3' exonuclease and a 3'→5' exonuclease. In some embodiments, exonucleases may be employed in which only functions exists, and other functions have been experimentally or naturally abolished. One non-limiting example of such a molecule is Klenow (5'→3' exo⁻) (which may also be written as Klenow ($Asp^{355}$; $Glu^{357}$; 5'→3' exo⁻), in which the 5'→3' exonuclease activity has been abolished, but the 3'→5' exonuclease activity of the enzyme is retained. Of course, for the purposes of the present disclosure, it will be readily appreciated by a practioner of ordinary skill in the art that additional endonucleases and exonucleases exist which, though not listed above, are suitable for use within the context of the present invention, without departing from the spirit and scope thereof, and that failure to list them above in no way precludes their use in one or more of the foregoing described embodiments.

As used herein, the term "secondary structure," when used in the context of a reference nucleic acid molecule, generally refers to the general three-dimensional form of local segments of nucleic acids (DNA/RNA). It does not, however, describe specific atomic positions in three-dimensional space, which are considered to be tertiary structure. Secondary structure is formally defined by the hydrogen bonds of the biopolymer, as observed in an atomic-resolution structure. In nucleic acids, the secondary structure is defined by the hydrogen bonding between the nitrogenous bases. The term may also be applied to describe various aspects of protein structure, however such an application is beyond the scope of the present disclosure and will thus not be considered further secondary structure occurs most notably in single-stranded nucleic acid (RNA and DNA) molecules. Secondary structure in nucleic acids may generally be divided into two broad categories: helices and various kinds of loops. Helices occur when two complementary or substantially complementary sequences that are present in the same nucleic acid molecule anneal (either by traditional Watson-Crick base pairing or, in the case of RNA, also by Hoogsteen base pairing). Typically, such helices form when a nucleic acid molecule has at least two complementary or substantially complementary sequences arranged either as everted repeats or as inverted repeats. Helices that form within the same nucleic acid molecule may also be said to be forming "intramolecular" base pairing. Thus, intramolecular base pairing may be differentiated from intermolecular base pairing, which occurs between two individual and separate complementary or substantially complementary nucleic acid molecules. The various types or unpaired loops that comprise secondary structures are generally found interspersed between helices. An example of a typical secondary structure is the stem-loop, in which a base-paired helix ends in an unpaired nucleic acid loop. Internal loops (short series of unpaired bases in a longer paired helix) and bulges (regions in which one strand of a helix has "extra" inserted bases with no counterparts in the opposite strand) are also frequent.

As used herein, the terms "nucleic acid ligand library," "nucleic acid library," "oligo library," "polynucleotide library," or the like, generally refer to a mixture of nucleic acid molecules having variable sequence from which to select an aptamer to a specific target molecule. The variable region will, for the purposes of the present disclosure, unless otherwise indicated, encompass the population of oligonucleotides having the sequence 5'-$N_x$-'3, where each N is independently A, G, C, or T (where T is replaced by U in the case where RNA is employed), and where x is an integer corresponding to the number of bases in the polynucleotide molecules of the library. Thus, for a polynucleotide library having whose constituent polynucleotide molecule have a length of about 1 kB, x is about 1000. In the case where the polynucleotide library comprises oligonucleotides, x will typically range from about 5 up to about 200, or up to about 150, or up to about 100, or up to about 50. In some non-limiting embodiments, x is between about 12 to about 25, or between about 15 to about 18. Thus, in this latter case there will exist in such a library between about $4^{15}$ to about $4^{18}$ unique oligonucleotide sequences. The constituent molecules of a nucleic acid ligand library may be naturally occurring nucleic acids or fragments thereof (such as is found, e.g., in a cDNA or EST library), chemically synthesized nucleic acids, enzymatically synthesized nucleic acids or nucleic acids made using any combination of the aforementioned techniques. In a subset of embodiments, each nucleic acid molecule in the library may include one or more fixed (e.g., known) nucleotide sequences 5' to, 3' to, or flanking, the variable region for the purpose of facilitating the enrichment and identification of target aptamers (such as by using PCR, affinity chromatography, or any similar methods used to purify or enrich target nucleic acids). In some embodiments, such fixed nucleotide sequences may be referred to as "adapters" or alternatively "tags." The sequence of the adapters used in the present description is entirely arbitrarily, chosen only for the purposes of clarifying the invention. It will be readily understood by the skilled artisan that other adapters may also be used, without departing from the spirit and scope of the embodiments set forth herein, the only limitation being that they are selected to be generally devoid of any secondary structure. One exemplary adapter sequence that may be used in accordance with the present embodiments is, by way of a first non-limiting example, the sequence 5'-GGGGGGGT-TGGTGGTTGGTN-3' (SEQ ID NO:1), where N is A, T, G, or C. Another exemplary adapter sequence that may be used in accordance with the present embodiments is, by way of a second non-limiting example, the sequence 5'-$N_y$-3', where N is A, G, C, T or, in the case of RNA, U, and where y is an integer from about 5 to about 25. In some embodiments, y may be from about 5 to about 50, or from 5 to about 100, or larger. An adapter may be synthesized as part of the oligonucleotide, or may be added to the oligonucleotide after the synthesis thereof. An oligonucleotide may be added, for example, by ligating one or more adapter sequences to the 5' or the 3' end of an oligonucleotide. Alternatively a poly-T adapter may be added to the 3' end of the nucleic acid oligonucleotides comprising the library using an enzyme such as terminal transferase (TdT) as a template independent polymerase that catalyzes the addition of deoxynucleotides to the 3' hydroxyl terminus of DNA molecules.

The term "amplifying," as used herein, generally refers to the duplication (by enzymatic means) of an oligonucleotide using a nucleotide polymerase enzyme such as DNA or RNA polymerase. Where amplification employs repetitive cycles of duplication such as using the "polymerase chain reaction," the polymerase is a heat stable polymerase such as the DNA polymerase of *Thermophilus aquaticus* (Taq).

The term "knockdown" is used herein to describe one process by which target-specific aptamers may be enriched from an oligonucleotide library. The term is meant to refer to the ability of target-bound aptamers to resist hydrolysis by various nucleases. Unbound oligonucleotides, on the other hand, are susceptible to enzymatic hydrolysis and their effective concentration is "knocked-down" in the presence thereof. The term, in the present context, is not to be confused with the unrelated process of RNA-interference (RNAi), which is sometimes also referred to as RNA-"knockdown."

"Contacting" in the context of target selection, generally refers to incubating an oligonucleotide library with target molecules. By "target molecule" is meant any molecule to which a specific aptamer selection is desired.

The term "target molecule" generally refers to any compound of interest for which an aptamer is desired. A target molecule may be a protein, a peptide (i.e., a 'small' protein), a carbohydrate, a polysaccharide, a glycoprotein, an hormone, a receptor, an antigen, an antibody, a virus, a prion, a substrate, a metabolite, a transition state analog, a cofactor, an inhibitor, a drug, a dye, a nutrient, a growth factor, an organic compound, or an inorganic compound, without limitation.

The term "binding buffer," when used in the context of binding a target molecule to an aptamer, generally refers to any suitable aqueous medium that enables or permits the interaction between a target molecule and an aptamer to occur. The composition of a binding buffer is not limited to any one particular formulation or component. On the contrary, the composition of a binding buffer may be tailored to a particular application or to a particular setting. In some embodiments, a binding buffer may be a physiologically hypertonic aqueous solution. In some embodiments, a binding buffer may be a physiologically hypotonic aqueous solution. In some embodiments, a binding buffer may be a physiologically isotonic aqueous solution. In one non-limiting embodiment, a binding buffer may be, e.g., a phosphate buffered solution. In an embodiment, a binding buffer may be, e.g., whole blood, fractionated blood, whole serum, or blood plasma. In one non-limiting set of embodiments, a binding buffer may typically comprise, e.g., about 1 mM to about 100 mM Tris, from about 10 mM to about 500 mM NaCl, from about 0.5 mM to about 50 mM KCl, from about 0.1 mM to about 10 mM $CaCl_2$. The pH of a binding buffer will generally be in the physiological range, e.g., preferably about 6-8, more preferably about 6.5-7.5, and most preferably about 7.0-7.5. Optionally, a binding buffer may include, for example, a carrier nucleic acid (e.g., from about 0.1 mg/ml to about 100 mg/ml tRNA) to prevent adsorption of library oligos to the wall of any vessel in which a screening procedure is being conducted. One non-limiting example of a typical binding buffer formulation suitable for the systems and methods described herein is 20 mM tris; 140 mM NaCl; 5 mM KCl, and 1 mM $CaCl_2$ and 10 mg/ml tRNA. The final components of a binding buffer ultimately vary, depending on a number of variables including but not limited to the identity and nature of the molecules involved, the equilibrium of the solution, and the relative binding affinity of the molecular association (typically denoted by a binding constant $K_d$). Secondary factors such as, e.g., the temperature of the system may also affect the binding conditions and thus selection of the constituents of a binding buffer. Optionally, agents such as ionic or non-ionic detergents, or other chaotropes, may be included in a binding buffer to influence the binding between a target and an aptamer (i.e., to insure that only high affinity aptamers are selected).

As used herein, the term "gene" generally refers to a functional unit of a polynucleotide molecule, typically a DNA molecule, which controls or influences one or more discreet, heritable and/or transferable phenotypes. Usually, though not exclusively, a gene corresponds to a single polypeptide or RNA, or isoforms thereof. A gene may designate an entire functional unit such as is found in the genome, including but not limited to coding regions (e.g. open reading frames), non-coding regulatory regions (e.g. promoters, enhancers, termination and polyadenylation signals, and the like) and introns. Alternatively, a gene may designate only portions or fragments thereof, such as, for example, a cDNA. A gene may be either chromosomal or extra-chromosomal. Furthermore, shuttle vectors are typically used to transfer isolated polynucleotides between cells of the same or different species. Viral vectors are typically packaged in viral coat proteins and are used for high efficiency transfection and/or expression of isolated polynucleotides in cells. In some cases, viral vectors will integrate into a host cell genome and become a transgene. Bacteriophage vectors are often used during gene cloning procedures (e.g., isolation and enrichment of polynucleotides). An ordinary practitioner of the art would readily appreciate however, that the aforementioned vector classifications are not mutually exclusive and that the placement of a vector in one of the aforementioned classifications does not preclude its placement in additional classifications. Rather, many vectors may be placed in a plurality of the aforementioned vector classifications. For example, subsets of expression vectors are also viral vectors, and subsets of expression vectors are also shuffle vectors. Additionally, many bacteriophage vectors are also cloning, shuttle and expression vectors. An "expression vector" is a nucleic acid construct, typically generated using recombinant DNA techniques, which contains a series of specified nucleic acid elements that permit transcription of a particular nucleic acid in a host cell. An expression vector may also optionally be adapted to allow for its integration and/or replication in a host cell. An expression vector may be part of a plasmid, a virus, or a nucleic acid fragment, of viral or non-viral origin. Typically, the expression vector includes an "expression cassette," into which may be inserted, using recombinant DNA techniques, an isolated polynucleotide that is to be expressed in a host cell. The isolated polynucleotide is operably-linked to one or more appropriate nucleic acid sequences that are necessary for or that augment the expression of the isolated polynucleotide in a particular host cell or organism. Nucleic acid sequences necessary for expression in prokaryotes usually include a promoter, an optional operator, and a ribosome binding site, often along with other sequences. Nucleic acid sequences necessary for the expression of a protein from an expression vector in eukaryotic cells include at least one promoter, termination and polyadenylation signals, and one or more optional enhancers.

GENERAL DESCRIPTION

Disclosed herein are novel methods of selecting aptamers that bind to a target molecule. Aptamers selected in accordance with the presently described embodiments may be selected in as few as 1 cycle of selection, or up to several hundred cycles of selection. Typically, aptamers selected in accordance with the presently described embodiments may be selected in up to about 15 cycles of selection. In some embodiments, aptamers selected in accordance with the presently described embodiments may be selected in about 1 to about 5 cycles, or in about 1 to about 3 cycles.

In an embodiment, a first cycle of aptamer selection may be performed at a first temperature, e.g., room temperature (about 20° C. to about 25° C.). The aptamers selected at the first temperature may then be subjected to a second round of selection. In an embodiment, the second round of selection may be carried out at a second temperature. The second temperature may be higher than, lower than, or substantially equal to the first temperature used to select the aptamers. Without being bound to any one particular theory or mechanism of action, and in full appreciation that other mechanisms of action not presently contemplated may be operative, increasing the temperature at which the aptamer is selected may increase the stringency of the screen for aptamers that bind to the target molecule. In an embodiment, a temperature at which a second round of selection may be performed may be in the range of, e.g., 27° C. to about 34° C.

The aptamers selected at the second temperature may then be subjected to a third cycle of selection. In an embodiment, the third cycle of selection may be carried out at a third temperature. The third temperature may be higher than, lower than, or substantially equal to the first or the second temperature used to select the aptamers. In an embodiment, the third temperature at which aptamers are selected may be substantially body temperature (i.e., around 37° C.). Again, without being bound to any one particular theory or mechanism, selecting aptamers at body temperature may select those aptamers that interact with the target molecule more efficiently and with greater affinity. Such aptamers are generally expected to have greater therapeutic utility in vivo. This may occur, for example because differences in the secondary structure of an aptamer, or in the tertiary structure of a protein target molecule, at body temperature enable them to interact with each more efficiently than they would at lower temperature.

It is desirable to provide an improvement over existing methods for selecting aptamers (e.g., by SELEX), since the method of isolating aptamers from unbound oligonucleotides does not require a step in which aptamers are physically separated from the oligonucleotide pool (such as, e.g., filtration, magnetic separation etc.). In this way, it is generally believed that the present invention may allow for the identification of weaker aptamers, i.e., those whose binding with the target molecule has a relatively low equilibrium constant, $K_{eq}$, and thus would otherwise be discarded.

An advantage of the method and system disclosed herein for selecting aptamers is that method does not require elaborate and expensive instrumentation. In contrast to methods such as SELEX, selection of aptamers in accordance with the presently described embodiments may be performed utilizing only a thermocyler and a benchtop centrifuge or vacuum manifold, all of which are standard equipment in most life science labs.

Disclosed herein is a method that utilizes a "two-pronged" strategy to enrich and amplify aptamers. For example, in an embodiment performed in accordance with the following description, aptamers may first be selected from an oligonucleotide library by subjecting oligonucleotide molecules that are not bound to the target to enzymatic hydrolysis. Bound oligonucleotides are then subject to PCR amplification and are then either identified and sequenced, or are subject to further rounds of enrichment and selection.

Disclosed herein is an efficient means of selecting aptamers under substantially physiological conditions (e.g., selecting in blood matrix, or selecting in blood matrix in conjunction with the physical separation tactics of SELEX).

Disclosed herein is a method that may be employed in conjunction with SELEX.

Still further embodiments concern kits suitable for the purpose of performing a screen for aptamers that bind to a molecule of interest. The kits include, in at least a first suitable container, a suitable oligonucleotide library, one or more endonucleases, and one or more 3'→5' exonucleases, in conjunction with instructions for use in performing a screen for aptamers that bind to a molecule of interest. A kit may optionally further contain one or more appropriate binding buffers, and/or one or more buffers suitable to enable activity of the provided nucleases. The kit may further contain one or more reagents, including suitable buffer, enzymes and primers, for amplifying selected aptamers by PCR.

DNA aptamers can be used in certain detection and identification systems for biological and chemical threat agents as well as for neutralization and therapeutics (Gray et al., 1998; Jayasena, 1999; Frauendork and Jaschke, 2001; Rajendron and Ellington, 2002; Wilson and Szostak, 1999). There is a need for new technologies to select and manufacture DNA aptamers which (1) address the mass action problem of weak binders competing out strong binders, (2) can save both time and expense in the biosynthetic methods employed in the Systemic Evolution of Ligands by Exponential enrichment (SELEX) method, and (3) can be miniaturized and packaged onto user friendly instruments. A method is therefore needed which DNA may rapidly and cost-effectively select aptamers with high binding affinity and high specificity, after only one or at most a few rounds of selection.

To address this technical hurdle, a method known as "Knockdown Nuclease Protected Aptamer Selection and Acquisition" (KN-PASA), which forms the basis of the present disclosure, is described herein. In KN-PASA, the resistance to hydrolysis by various nucleases of a target-bound aptamer is exploited as a method to separate target-bound aptamers from unbound oligonucleotides, without having to subject the complexes to a physical enrichment step. In this way, KN-PASA may, at least in part, address and overcome many of the difficulties associated with aptamer selection methods (e.g., SELEX) that do require a separation step. Without being bound to any specific theory or mechanism, knockdown of weak binders by endonucleases such as T7 Endonuclease 1 may, at least in some embodiments, mitigate some of the issues with mass action that are frequently encountered with current aptamer selection methods. Consequently, aptamers may be selected by KN-PASA in only one to three cycles. Moreover, since KN-PASA uses only nuclease digestion and PCR technology, the need for highly specialized equipment is obviated. The only equipment required of the present method is a PCR thermocycler and a centrifuge or vacuum manifold (e.g., for columns).

Turning to FIG. 1, a first step in performing KN-PASA may include incubating a target molecule of interest with nucleic acid ligand library under conditions (e.g., at room temperature or higher) that would allow binding of the target molecule to one or more aptamers present in the nucleic acid ligand library. Typically the target molecule will be at least partially purified and dissolved in an appropriate aqueous medium, such as an appropriate binding buffer. Typically, with oligonucleotide in the library will bear, at least on the 5' terminal, one or more adapter sequences. Thus, in FIG. 1A, a target molecule (e.g., thrombin) is contacted with a nucleotide candidate library. In the non-limiting case shown in FIG. 1A, thrombin is used, however, it is to be understood that the use of thrombin herein is for the purpose of illustration only and is non-limiting for the present methods. KN-PASA is equally applicable to any target molecule without limitation.

Figure 1A:
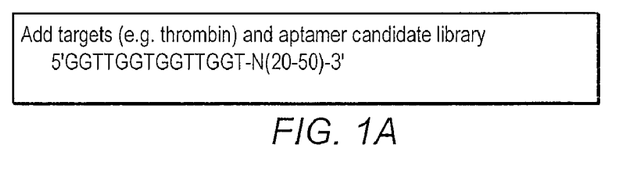

The library depicted in this embodiment includes a variable region having the sequence 5'-$N_{20-50}$-3' having the 5' adapter sequence shown in FIG. 1A attached to the 5' end thereof. The adapter shown here is a single tandem repeat comprising the sequence 5'-GGTTGGTGGTTGGT-3' (SEQ ID NO:2). It is to be understood however that any adapter that is substantially devoid of secondary structure is equally suitable for the present purposes. The 5' adapter, which lacks secondary structure, is resistant to certain nuclease, e.g., Exonuclease I and Exonuclease T degradation when the aptamer is target-bound, as these enzymes hydrolyze phosphodiester bonds of single stranded DNA in the 3'→5' direction.

Figure 1B:
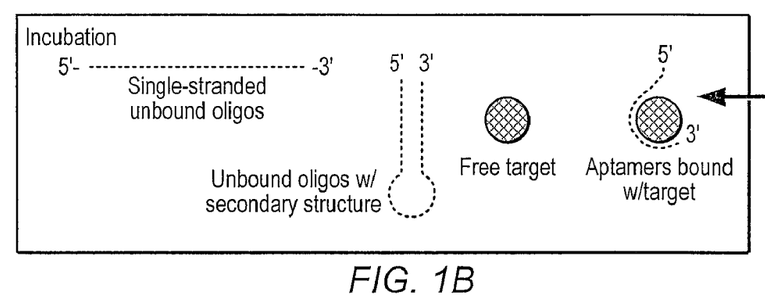

In one embodiment, the target molecule is incubated with the nucleic acid ligand library in binding buffer and at temperature in the range of about 18° C. to about 45° C. for a period ranging from about 5 minutes to generally not longer than about 48 hours. In most cases, the incubation step should be accomplished in less than 5 hours, more typically, less than 2 hours. Turning now to FIG. 1B, it can be seen that the incubation step results in a variety of products including but not limited to a) unbound single-stranded oligos, b) unbound oligos having secondary structure, c) unbound target molecule, and d) aptamer-bound target.

Figure 1C:
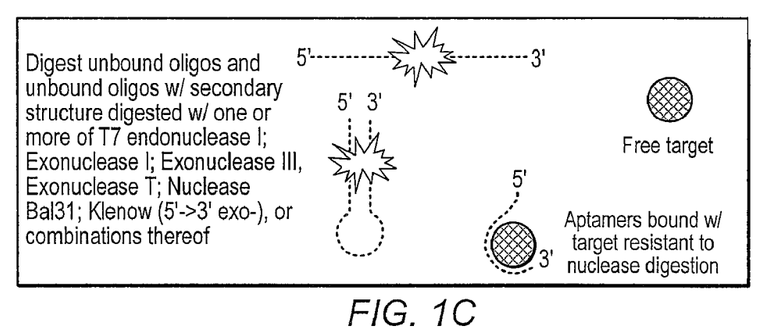

The goal of KN-PASA is to subtract (i.e., knock-down) the unbound single-stranded oligonucleotides and unbound oligonucleotides having secondary structure. In an embodiment, separation of the unbound single-stranded oligos and unbound oligos having secondary structure from target-bound aptamers may be accomplished by adding one or more nucleases to the mixture resulting in the step depicted in FIG. 1B, thereby enriching target bound aptamers. In one embodiment, enrichment of target-bound aptamers may be accomplished by adding to the mixture depicted in FIG. 1B one or more endonucleases, one or more exonucleases, or one or more endonucleases in combination with one or more exonucleases. Endonucleases suitable for use in the present embodiments may include, though are not limited to DNase I, S1 Nuclease, Nuclease Bal31, Mung bean nuclease, and T7 endonuclease I. In certain embodiments, one or more exonucleases having 3'→5' activity may be employed. As depicted in FIG. 1C, single-stranded unbound oligonucleotides by be digested (knocked-down) using for example, exonuclease I, exonuclease T, or their combination. Unbound oligonucleotides having secondary structure may be hydrolyzed using any enzyme that acts on intramolecular secondary structure including, by way of non-limiting example, any 3'→5' exonuclease such as one or more of Exonuclease III, Lambda Exonuclease, Nuclease Bal-31, T7 Exonuclease, T7 Endonuclease I and Klenow (5'→3' exo⁻), or combinations thereof. As is depicted in FIG. 1C, target-bound aptamers are resistant to nuclease digestion and are thereby enriched in solution.

In a next step, selected or enriched aptamers are liberated from the target molecule. This may be accomplished using any method of disrupting intermolecular hydrogen bonding, such as by, e.g., subjecting the sample containing aptamer bound target to denaturing conditions (e.g., heat denaturation, addition of detergents or chaotropes, phenol extraction, and the like). In the case of heat denaturation, the sample may be subjected to up to 100° C. for 10 seconds to 10 min. Optionally the enriched aptamers may be subjected to one or more rounds of selection under more stringent conditions (lower ionic strength, higher temperature etc.), and subjected to further nuclease degradation in one or more additional enrichment cycles. For example, in an embodiment, second or subsequent rounds of selection may be conducted at 30° C. rather than 22° C.

After the initial nuclease-based knockdown enrichment, the aptamer candidates may be tagged at their 3' end with a tag suitable for amplification. In one non-limiting embodiment, a suitable tag (e.g., a poly-T tag) may be easily attached to the 3' tail of aptamer candidates using the enzyme Terminal Transferase (see FIG. 1D) to add a 3' poly-T adapter. PCR utilizing primers targeting the 5' and 3' adapters may then be used to amplify the selected aptamer candidates for further enrichment cycles (see FIG. 1D'). Prior to subjecting the selected aptamer candidates to further enrichment cycles, the double-stranded amplicons comprising the aptamer candidate pool may first be denatured single-stranded molecules. The term "denature," when used in the context of nucleic acids, generally refers to the reversible generation of two constituent single-stranded nucleic acid structures from a double stranded nucleic acid structure (i.e., by disrupting hydrogen bonds of complementary nucleotide bases). Exemplary methods for denaturing nucleic acids include, though are not limited to, heat denaturation and alkaline denaturation. In heat denaturation, nucleic acid molecules are heated to a temperature that exceeds the melting temperature ($T_m$) of the double-stranded nucleic acid. In alkaline denaturation, the pH of the aqueous solution in which the double stranded nucleic acid is dissolved is elevated (such as, e.g., by the addition of exogenous hydroxide) to higher than the alkaline transition pH for the nucleic acid molecule. The term may be used in reference to either DNA or RNA, and may further be used in reference to intermolecular or intramolecular separation into two single strands. The reverse process (i.e., forming a double stranded nucleic acid structure from two complementary single-stranded nucleic acid structures) is generally referred to as "annealing." After the final round of aptamer selection, the double-stranded aptamer candidate may be sequenced, and the strand to which the target molecule binds may be identified by preparing single-stranded oligonucleotides corresponding to each strand, and independently testing their ability to bind to the target molecule.

Figure 1D:
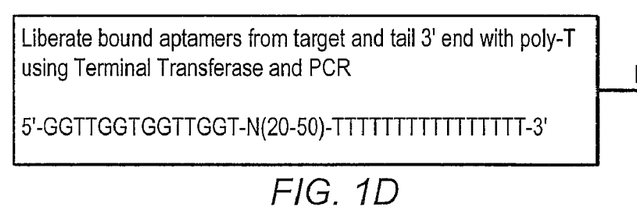
Figure 1E:
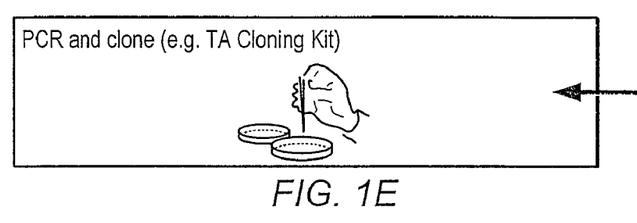

The two-pronged enrichment strategy is accomplished by alternating nuclease knockdown of non-binders with PCR amplification of binders (see FIG. 1D"). Up to three enrichment cycles, or more, may be performed. In one embodiment, a first round of selection with incubation and nuclease hydrolysis at room temperature (25° C.=RT), is performed, followed by a second round of selection at 31° C. and then followed with a final round of selection at 37° C. As discussed above, aptamers selected from a 37° C. cycle may be more likely to have therapeutic utility in vivo. Finally, aptamer candidates, from the three families of enrichment cycles, are acquired by ligation into an appropriate cloning vector (e.g., TA or TOPO Cloning Vector) and transformed using standard laboratory protocol into competent *E. coli* from which recombinant plasmids are recovered and sequenced. The aptamers that are selected are then further characterized for binding affinity and specificity. The enrichment cycling is a two-pronged approach that "knocks down" unbound oligos with nucleases and "knocks up" binders by PCR amplification. Using, this two-pronged enrichment approach, which does not require that non-binding oligos be physically separated from target bound oligos, is likely to yield a greater number of aptamer candidates than utilizing SELEX alone. Furthermore, because of the relative ease and adaptability of the present methods, the use thereof in conjunction with other SELEX protocols is equally contemplated.

EXAMPLES

Having now described the invention, the same will be more readily understood through reference to the following example(s), which are provided by way of illustration, and are not intended to be limiting of the present invention.

Example 1

Exonuclease I may, in some embodiments, be used to hydrolyze unbound oligos lacking secondary structure (Lehman and Nussbaum, 1964; Goldmark and Linn, 1972; Rosamond et al., 1979). One Unit of Exonuclease I is defined as the amount of enzyme that will catalyze the release of $6 \times 10^{15}$ bases in 30 minutes at 37° C. A first embodiment may begin with about 1.0 nmol of oligonucleotide library. The number of bases this represents can be calculated as follows: $((6 \times 10^{23}\ \text{molecules/mole}) \times (10^9\ \text{moles}) \times (100\ \text{bases/molecule})) = 6 \times 10^{16}$ bases. 10 Units of Exonuclease I should completely hydrolyze the aptamer candidate library if they lacked secondary structure. This enzyme is available from New England Biolabs at 20 or 200 Units per µl.

T7 Endonuclease I may, in some embodiments, may be used to hydrolyze unbound oligos having secondary structure (Xu and Evans, 2001; Parkinson and Lilley, 1997; White et al., 1997; Hadden et al., 2001). 1 Unit of T7 Endonuclease I hydrolyzes 1 µg of supercoiled cruciform pUC(AT) to >90% linear form in a total reaction volume of 50 µl in 1 hour at 37° C. One embodiment may begin with 1 nmol of oligonucleotide library. The weight of the starting material can be calculated as follows: $((30{,}000\ \text{g/mole}) \times (10^{-9}\ \text{mole})) = 3 \times 10^{-5}$ g. 150 Units of T7 Endonuclease I should completely hydrolyze the aptamer candidate library if they all had secondary structure. This enzyme is available from New England Biolabs at 20 or 200 Units per µl.

As the above calculations show, in theory, a single cycle of Exonuclease I and T7 Endonuclease I degradation will be required to hydrolyze the target below the threshold of PCR amplification. In practice it may require more than one cycle and this has yet to be determined. If required, this cycling will be accomplished by liberating aptamers from thrombin with increased temperature and passing the reaction, after the first digestion, through Qiagen's Nucleotide Removal Kit (Cat. No. 28304) with a buffer exchange (See FIG. 2). This column is designed for the removal of primers less than 10-mer, proteins, salts and unincorporated nucleotides. Oligos of 15-mer and larger are retained. After clean up, incubation with thrombin will be reestablished under more stringent conditions (e.g. higher temperature) and the nuclease degradation step is repeated. In an embodiment, aptamers flay be selected with three cycles, one at RT, one at 31° C. and one at 37° C.

T7 Endonuclease I may hydrolyze the secondary structure of target-bound aptamers having a loose association with thrombin or other targets of interest. This means that some perfectly good aptamers will be lost. On the other hand, one might predict that these aptamers do not have the binding affinity and specificity of bound aptamers that are resistant to hydrolysis by T7 Endonuclease I. As noted above, the law of mass action makes it difficult to select against weak binders with a single cycle of SELEX. The action of T7 Endonuclease I on weakly associated binders may reduce this technical barrier, providing a major opportunity to select good aptamers with many fewer cycles than are required by SELEX. If aptamer recovery is not accomplished in 1 to 3 cycles, KN-PASA may be performed for up to about 15 rounds of selection and amplification or more, if conditions warrant.

Example 2

PCR Control

To amplify by PCR and clone oligonucleotide aptamers selected in accordance with KN-PASA, primers targeting the 5' and 3' "tags". Shown below is a hypothetical aptamer selected in accordance with the above, having the 5' tag and 3' poly-T tags (both underlined) and will mimic the actual targets of a K-PASA assay.

(SEQ ID NO:3)
Aptamer-5'<u>GGTTGGTGGTTGGTGGTTGGT</u>GTGGTGGGGGGGGGGGGGG

GGGGGGGGGGGGGGGGGGGGGGGGGGGGG<u>TTTTTTTTTTTTTTTT</u> 3'

1. PCR using the upper primer 5'GGGGTTGGTGGTTG-GTN3' (SEQ ID NO:4) and the lower primer 5'-AAAAAAAAAAAAAAAAAAAA-3 (SEQ ID NO:5)

Materials and Methods

To a 200 µl thin walled PCR tube: Add 0.01 pmol of "Aptamer" Add 20 of 10 PCR Buffer
Add 2 µl of upper primer (2 µM)
Add 2 µl of lower primer (2 µM) Add 1.6111 of dNTP (25 µM)
Add 1 µl of Taq (5 U/µl) QS to 20 µl with $H_2O$
Thermocycle: (94° C. for 30 sec.→40° C. for 2 min.→72° C. for 30 sec. for 30 cycles)→72° C. for 5 min.→hold at 4° C.

Visualize presence of appropriate amplicons on ethidium bromide stained agarose or polyacrylamide gel. If amplicons are present, clone into Invitrogen TA Cloning vector, transform and grow competent cells, plate and pick colonies, miniprep colonies and sequence.

Note: Visualizing small amplicons is often difficult by Ethidium Bromide/UV illumination. It may be necessary to visualize perform the above PCR using one or more radionuclide-labeled dNTS such as, $[\alpha\text{-}^{32}P]$-dCTP and exposing the gel-resolved amplicons to film autoradiography.

Include negative controls (One lacking aptamer and one lacking primers).

Example 3

The conditions necessary for Exonuclease I to hydrolyze a single stranded target lacking secondary structure are examined here. Shown below is a hypothetical aptamer selected in accordance with the above, having the 5' tag and 3' poly-T tags. It may require several coupled nuclease cycles to knockdown the oligos below the threshold of amplification (See FIG. 2).

Aptamer:
(SEQ ID NO:6)
5'GTTGGTGGTTGGTGGTTGGTGTGGTTGGGGGGGGGGGGGGGGGGGG

GGGGGGGGGGGGGGGGGGGTTTTTTTTTTTTTTTT-3'

Materials and Methods
To a 200 µl thin walled PCR tube:
Add 1.0 pmol of "aptamer"
Add 20 Units of Exonuclease I
Add 2 µl of 10× Exonuclease I Buffer QS to 20 µl with H₂O Incubate at 37° C. for 2 hrs, followed by a heating step at 80° C. for 15 minutes to inactivate the Exonuclease I.

PCR as above using the primers 5'-GGGGTTGGTGGT-TGGT-3' (SEQ ID NO:23) and 5'AAAAAAAAAAAA-AAAAAAA-3'(SEQ ID NO:5)

Note: Exonuclease I and Exonuclease T may also be utilized in this step according to some embodiments.

Thermocycle: (94° C. for 30 sec.→40° C. for 2 min.→72° C. for 30 sec. for 30 cycles)→72° C. for 5 min.→hold at 4° C. Check for amplicons on an agarose gel. No amplicons are expected in this example. Positive Control: Omit Exonuclease. Negative Controls: Omit Aptamer Probe (Target), Omit Primers.

Example 4

In this example, the conditions necessary for Exonuclease I or Exonuclease T and T7 Endonuclease I to hydrolyze 2 single stranded targets having secondary structure are determined.

One aptamer target is:

(SEQ ID NO:7)
5'GGTTGGTAAAAAAAAAAAAAAGGGGGGGGGGGGGGGGGGGGGGGG

GGGGGGGGGGGGGGGTTTTTTTTTTTTTTTGGTTGGT3'

This target has single stranded termini and internal double stranded structure. The primers used in the PCR are:

```
5'GGTTGGTAAAAAAAAAAAAAA3'        (SEQ ID NO:8)
and

5'ACCAACCAAAAAAAAAAAAAAAA3'      (SEQ ID NO:9)
```

The second aptamer is:

(SEQ ID NO:10)
5'AAAAAAAAAAAAAAGGTTGGTGGGGGGGGGGGGGGGGGGGGGGGG

GGGGGGGGGGGGGGGGTTGGTTTTTTTTTTTTTTTTT3'

This target has double stranded termini.

The primers used in the PCR:

```
5'AAAAAAAAAAAAAAGGTT3'           (SEQ ID NO:11)
and

5'AAAAAAAAAAAAAAAACCAACCCC3'     (SEQ ID NO:12)
```

Materials and Methods

To a 200 µl thin walled PCR tube:
  Add 1.0 nmol of appropriate aptamer target
  Add 1 µl of 10× Exonuclease I Buffer
  Add 1 µl of 10 T7 Endonuclease I Buffer
  Add 20 Units of Exonuclease I
  Add 200 Units of T7 Endonuclease I
  QS to 20 µl with H₂O Incubate at 37° C. for 2 hrs.

For PCR:
  Add 5 µl of Exonuclease Digested Reaction from above
  Add 2 µl of 10×PCR Buffer
  Add 2 µl of upper primer (2 µM)
  Add 2 µl of lower primer (2 µM)
  Add 1.6 µl of dNTP (25 µM)
  Add 200 U of Taq (5 U/µl)
  QS to 20 µl with H₂O
  Thermocycle: (94° C. for 30 sec.→40° C. for 2 min.→72° C. for 30 sec. for 30 cycles)→72° C. for 5 min.→hold at 4° C. Positive Control: Omit Exonucleases Check for amplicons on an agarose gel. Amplicons are expected. If amplicons are present, clone into Invitrogen TA Cloning vector, transform and grow competent cells, plate and pick colonies, miniprep colonies and sequence. If amplicons are not recovered, optimize the Terminal Transferase tailing reaction.

Negative control: Omit tailing step and try to amplify with 5'GGTTGGTGGTTGGTGTGTGGTT3'(SEQ ID NO: 13) and 5'AAAAAAAAAAAAAAAA3' (SEQ ID NO:14); Omit primers and try to amplify; Omit target and attempt PCR.

Note: During the enrichment cycle, amplified aptamer candidates that are redigested by nucleases will likely need to be "re-tailed" with 3' poly-T before subsequent amplifications as the poly-T tail could be subject to exonuclease degradation.

Example 5

In this specific aim, we will use the thrombin aptamer probe reported by Wang et al. (2004), with a slight modification, to see if we can recover it using K-PASA. The modification is a single tandem repeat of the 5' adapter used by Wang et al. (2004). This tandem repeat provides the upper priming site for the PCR step.

The aptamer to be tested will be 5 GGTTGGTGGTTGGTG-GTTGGTGTGGTTGG3'(SEQ ID NO:15)

After the nuclease protection cycling is performed, Terminal Transferase will be used to tail the aptamer with polyT so that the aptamer may be amplified by PCR using the following primers 5'GGGGGGGTTGGTGGTTGGTN3'(SEQ ID NO:16) and 5'AAAAAAAAAAAAAAAAAAAAB3'(SEQ ID NO:17). In the positive control, the nuclease degradation step is omitted.

Materials and Methods

To a 200 µl thin walled PCR tube:
  In 10 µl of binding buffer (20 mM Tris-HCl, 140 mM NaCl, 5 mM KC, 1 mM CaCl₂, 10 mg/ml tRNA);
  Add 1.0 pmol Thrombin
  Add 1.0 pmol of "aptamer probe" Allow binding for 1 hr. at RT Add 20 Units of Exonuclease I
  Add 2 µl of 10× Exonuclease I Buffer
  QS to 20 µl with H₂O
  Incubate at RT for 2 hrs, followed by a heating step at 80° C. for 15 minutes to inactivate the Exonuclease I and liberate bound aptamers.

Note: For enrichment, the above cassette can be cycled at progressively more stringent conditions, for example, by raising the incubation temperature as well as by amplifying the "survivors" by PCR cycling as described in detail above. The initial incubation will be done at RT and subsequent incubation cycling will be done at 31° C. and 37° C. Aptamers that are able to bind at 37° C. are more likely to have in vivo therapeutic utility. Exonuclease I is optimized for use at 37° C. For lower temperatures, incubations will be adjusted, according to enzyme Q10 rules, by increasing incubation time and/or enzyme concentration.

Attempt to Recover Aptamer:

To a 200 µl thin walled PCR tube:
  Add 5 µl of Exonuclease Digested Reaction from above.
  Add 2 µl of 10×PCR Buffer Add 2 μl of upper primer (2 μM)
Add 2 μl of lower primer (2 μM)
Add 1.6 μl of dNTP (25 μM)
Add 1 μl of Taq (5 U/μl)
QS to 20 μl with $H_2O$
Thermocycle: (94° C. for 30 sec.→40° C. for 2 min.→72° C. for 30 sec. for 30 cycles)→72° C. for 5 min.→hold at 4° C.

Check for amplicons on an agarose gel. Amplicons are expected. If amplicons are present, clone into Invitrogen TA Cloning vector, transform and grow competent cells, plate and pick colonies, miniprep colonies and sequence. If amplicons can't be recovered, optimize assay. As a positive control, omit nucleases. As a negative control, omit Thrombin.

Example 6

In this example, aptamers against Thrombin are selected and acquired from an oligonucleotide library of 5'GGTTG-GTGGTTGGTN$_{30}$-3' (SEQ ID NO:18).

Materials and Methods
To a 200 μl thin walled PCR tube:
In 10 μl of binding buffer (20 mM Tris-HCl, 140 mm NaCl, 5 mM KCl, 1 mM $CaCl_2$, 10 mg/ml tRNA),
Add 1.0 nmol Thrombin
Add 1.0 nmol of "aptamer probe"
Allow binding for 1 hr. at RT
Add 1 pl of I0× Exonuclease I Buffer
Add 1 μl of I0×T7 Endonuclease I Buffer
Add 20 Units of Exonuclease I
Add 200 Units of T7 Endonuclease I
QS to 20 μl with $H_2O$
Incubate at RT for 2 hrs, followed by a heating step at 80° C. for 15 minutes to inactivate the exonucleases and liberate bound aptamers.

Note: For enrichment, the above cassette can be cycled at progressively more stringent conditions, for example, by raising the incubation temperature as well as by amplifying the "survivors" by PCR cycling. The initial incubation will be done at RT and subsequent incubation cycling will be done at 31° C. and 37° C. Aptamers that are able to bind at 37° C. are more likely to have in vivo therapeutic utility. These exonucleases are optimized for use at 37° C. For lower temperatures, incubations will be adjusted, according to enzyme Q10 rules, by increasing incubation time and/or enzyme concentration.

Liberate Aptamers from Thrombin and Pass through Qiagen Nuclease Removal Kit.
Tail Aptamers with Poly-T Using Terminal
Transferase:
To a 200 μl thin walled PCR tube:
Add 10 μl eluant from above.
Add 2 μl of 10× Terminal Transferase Buffer
Add 20 Units of Terminal Transferase
Add 1 μl of dTTP (10 μm)
QS to 20 μl with $H_2O$ Incubate at 37° C. for 20 min.
Heat inactivate Terminal Transferase at 75° C. for 20 min.
Attempt to amplify the aptamer by PCR using the following primers

```
5'GGGGGGGTTGGTGGTTGGTN3'      (SEQ ID NO:19)
and

5'AAAAAAAAAAAAAAAAAAAB3':     (SEQ ID NO:17)
```

Perform PCR
Add 5 μl of Terminal Transferase Reaction from above.
Add 2 μl of 10×PCR Buffer
Add 2 μl of upper primer (2 μM)
Add 2 μl of lower primer (2 μM)
Add 1.6 μl of dNTP (25
Add 1 μl of Taq (5 U/μl)
QS to 20 μl with $H_2O$
Thermocycle: (94° C. for 30 sec.→40° C. for 2 min.→72° C. for 30 sec. for 30 cycles)→72° C. for 5 min.→hold at 4° C. Check for amplicons on an agarose gel. If amplicons are present, clone into Invitrogen TA Cloning vector, transform and grow competent cells, plate and pick colonies, miniprep colonies and sequence. As a positive control, omit nucleases. As a negative control, omit Thrombin.

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the claims appended hereto.

REFERENCES

Bruno J G, Kiel J L, "Use of magnetic beads in selection and detection of biotoxin aptamers by electrochemi-luminescence and enzymatic methods", Biotechniques, 32(1.):178-80, 182-3, 2002.

Bruno J G and Kiel J L, "In vitro selection of DNA aptamers to anthrax spores with electronchemi-luminescence detection", Biosen & Bioelectro, 14, 457, (1999).

Chambers, J. P., Valdes, J. J., and Goode, M. T., "Aptamer-Based, High Throughput MEMS Sensor for Automated Screening and Detection of Biological Threat Agents", Presented at the 2001 Scientific Conference on Chemical and Biological Defense Research, Mar. 6-8, 2001.

Chambers, J. P., and Valdes, J. J., "In Vitro Selection of Lysozyme Specific Aptamers on silicon Chips", Poster presentation, 23rd Army Science Conference, Dec. 2-5, 2002.

Cox J C, Rajendran M, Riedel T, Davidson E A, Sooter L J, Bayer T S, Schmitz-Brown M, Ellington A D. "Automated acquisition of aptamer sequences", Comb Chem High Throughput Screen, 5(4):289-99, 2002a.

Cox J C, Hayhurst A, Hesselberth J, Bayer T S, Georgiou G, Ellington A D, Automated selection of aptamers against protein targets translated in vitro: from gene to aptamer", Nucleic Acids Res, 30(20):2002b.

Cox J C and Ellington A D, "Automated selection of anti-protein aptamers", Bioorg Med Chem; 9(10), 2525-31, 2001.

Andrew D. Ellington, J. Colin Cox, Letha Sooter, Travis Bayer, Gwen Motz, Allysia Hood, Carlos Garcia, Jay Hesselberth, Brad Hall, Fang en Lee, Matt Levy, Manjula Rajendran, Romy Kirby, Brian Gehrke, Jim Collett, Scott Knudsen, and Seth Cockrum. Automated generation of nucleic acid biosensors for biothreat agents. 2002 23rd Army Science Conference, Transformational Science and Technology for the Army . . . a race for speed and precision. KO-05.

Frauendork C., and Jaschke A., "Detection of small organic analytes by fluorescing molecular switches", Bioorg MEd Chem, 9, 2521, (2001).

Gold L, Polisky B, Uhlenbeck 0, Yarns M. Diversity of oligonucleotide functions. Annu Rev Biochem. 1995; 64:763-97.

Goldmark P J, Linn S. Purification and properties of the recBC DNase of *Escherichia coli* K-12. J Biol Chem. 1972 Mar. 25; 247(6):1849-60.

Gray N S, Wodicka L, Thunnissen A M, Norman T C, Kwon S, Espinoza F H, Morgan D O, Barnes G, LeClerc S, Meijer L, Kim S H, Lockhart D J, Schultz P G. (1998) Exploiting chemical libraries, structure, and genomics in the search for kinase inhibitors. Science 281, 533-538.

Grossowicz, N., Ariel, M. and Weber, T. (1979) Clin. Chem. 25: 484-485.

Hadden J M, Convery M A, Declais A C, Lilley D M, Phillips S E. Crystal structure of the Holliday junction resolving enzyme T7 endonuclease I. Nat Struct Biol. 2001 January; 8(1):62-7.

Hesselberth J, Robertson M P, Jhaveri S, and Ellington A D, "In vitro selection of nucleic acids for diagnostic applications", Rev Mol Biotech, 74, 15, (2000).

Hybarger G, Bynum J, Williams R F, Valdes J J, Chambers J P, "A microfluidic SELEX prototype", Anal Bioanal Chem, 384(1):191-8, (2006).

Irvine D, Tuerk C, Gold L., SELEXION: Systematic evolution of ligands by exponential enrichment with integrated optimization by non-linear analysis. Mol. Biol., 222:739-761, 1991.

Iqbal, S. S., Chambers, Brubaker, R. R., J. P., Goode, M. T., and Valdes, J. J., "Detection of *Yersinia pestis* using branching DNA", Mol Cellular Probes, 13, 315, (1999).

Igbal, S. S., Mayo, M. M., Bruno, J. G., Bronk, B. V., Batt, C. A., and Chambers, J. P., "A review of molecular recognition technologies for detection of biological threat agents", Biosen & Bioelectro, 15, 549, (2000a).

Iqbal, S. S., Chambers, J. P., Goode, M. T., Valdes, J. J., and Brubaker, R. R., "Detection of *Yersinia pestis* by pesticn fluorogenic probe-coupled PCR", Mol Cellular Probes, 14, 109, (2000b).

Iqbal, S. S, Yalavarthi, S., Valdes, J. J, and Chambers, J. P., "Biopanning for Lysozyme Specific Aptamers Using Micro-Electro-Mechanical Silicon Chips" Bioelect & Biosensors, in press (2003).

Jayasena S D. Aptamers: an emerging class of molecules that rival antibodies in diagnostics. Clin Chem. 1999 September; 45(9):162850.

Jhaveri, S., Rajendran, M., and Ellington, A. D., "In vitro selection of signaling aptamers", Nat Biotech, 18, 1293, (2000).

Klug S. J. and Famulok M., All you wanted to know about SELEX. Mol. Biol. Reports 20: 97-107, 1994.

LEHMAN I R, NUSSBAUM A L. THE DEOXYRIBONUCLEASES OF *ESCHERICHIA COLI*. V. ON THE SPECIFICITY OF EXONUCLEASE I (PHOSPHODIESTERASE). J Biol. Chem. 1964 August; 239:2628-36.

Parkinson M J, Lilley D M. The junction-resolving enzyme T7 endonuclease I: quaternary structure and interaction with DNA. J Mol Biol. 1997 Jul. 11; 270(2):169-78.

Rajendran M, Ellington A D. Selecting nucleic acids for biosensor applications. Comb Chem High Throughput Screen. 2002 June; 5(4):263-70.

Rosamond J, Telander K M, Linn S. Modulation of the action of the recBC enzyme of *Escherichia coli* K-12 by $Ca^{2+}$ J Biol Chem. 1979 Sep. 10; 254(17):8646-52.

Vivekananda J, Kiel J L, "Anti-Francisella tularensis DNA aptamers detect tularemia antigen from different subspecies by Aptamer-Linked Immobilized Sorbent Assay", Lab Invest, 86(6): 610-8 (2006).

Wang X-L, Li F, Su Y-H, Sun X, Li X-B, Schluesener H J, Tang F and Xu S-Q, "Ultrasensitive Detection of Protein Using an Aptamer-Based Exonuclease Protection Assay", Anal Chem., 76(19), 5606, (2004).

White M F, Giraud-Panis M J, Pohler J R, Lilley D M. Recognition and manipulation of branched DNA structure by junction resolving enzymes. J Mol Biol. 1997 Jun. 27; 269(5):647-64. Review.

Wilson D S, Szostak J W. In vitro selection of functional nucleic acids. Annu Rev Biochem. 1999; 68: 611-47.

Xu M Q, Evans T C Jr. Intein-mediated ligation and cyclization of expressed proteins. Methods. 2001 July; 24(3):257-77. Review.

What is claimed is:

1. A method of identifying nucleic acid aptamers for a target molecule comprising: obtaining an at least partially purified target molecule; obtaining a nucleic acid ligand library, said nucleic acid ligand library comprising a plurality of nucleic acid molecules; mixing the target molecule with the nucleic acid ligand library such that the target molecule binds to one or more aptamers present in the nucleic acid ligand library; digesting unbound nucleic acid molecules with one or more endonuclease, with one or more exonucleases, or with one or more endonuclease in combination with one or more exonucleases.

2. The method in accordance with claim 1, wherein the nucleic acid ligand library comprises a plurality of nucleic acid molecules comprising the sequence 5'-$N_x$-3', where each N is independently A, C, G, T or, U, and where x is an integer ranging from about 5 to about 1000.

3. The method in accordance with claim 1, wherein the mixing step is carried out at substantially room temperature.

4. The method in accordance with claim 1, wherein the mixing step is carried out for up to about 5 hours.

5. The method in accordance with claim 1, wherein the mixing step is carried out in a binding buffer, said binding buffer comprising one of a physiologically hypertonic aqueous solution, a physiologically hypotonic aqueous solution, or a physiologically isotonic aqueous solution.

6. The method in accordance with claim 5, wherein the pH of said binding buffer is between about 6 to about 8.

7. The method in accordance with claim 5, wherein the binding buffer comprises at least one composition selected from the list consisting of Tris, NaCl, KCl, $CaCl_2$, and tRNA, or combinations thereof.

8. The method in accordance with claim 1, further comprising liberating the aptamer from the target molecule.

9. The method in accordance with claim 8, wherein said liberating step comprises heat denaturation and a temperature up to about 100° C.

10. The method in accordance with claim 8, further comprising adding an adapter to the 3' of the liberated aptamer.

11. The method in accordance with claim 10, wherein the adapter comprises the nucleotide sequence $N_x$, where N is selected from the nucleotide A, T, C, or G, and wherein x is an integer from about 5 to about 30.

12. The method in accordance with claim 10, wherein the liberated aptamers are amplified by PCR.

13. The method in accordance with claim 1, wherein one or more of the exonucleases are 3'→5' exonucleases.

14. The method in accordance with claim 1, wherein the digesting step is carried out with one or more of Exonuclease I, Exonuclease T, Exonuclease III, T7 Endonuclease I, or combinations thereof.

15. The method in accordance with claim 1, wherein the nucleic acid molecules comprising the nucleic acid ligand library further comprise a 5' adapter sequence, a 3' adapter sequence, or a 5' and a 3' adapter sequence.

16. The method in accordance with claim 15, wherein the adapter sequence comprises at least a portion of the nucleotide sequence GGTTGGTGGTTGGTG (SEQ ID NO:20).

* * * * *